(12) United States Patent
Strittmatter et al.

(10) Patent No.: US 7,090,986 B2
(45) Date of Patent: Aug. 15, 2006

(54) PROTEIN FOR BLOCKING PLATELET ADHESION

(75) Inventors: Wolfgang Strittmatter, Ober-Ramstatt (DE); Detlef Güssow, Darmstadt (DE); Uwe Hofmann, Alsbach (DE); Jürgen Hemberger, Aschaffenburg (DE); Zisi Fotev, Bickenbach (DE); Bernhard Scheuble, Seeheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 11/153,433

(22) Filed: Jun. 16, 2005

(65) Prior Publication Data

US 2006/0094079 A1    May 4, 2006

Related U.S. Application Data

(60) Division of application No. 10/846,668, filed on May 17, 2004, now Pat. No. 6,962,801, which is a continuation of application No. 09/936,737, filed as application No. PCT/EP00/02117 on Mar. 10, 2000, now Pat. No. 6,774,107.

(30) Foreign Application Priority Data

Mar. 18, 1999 (EP) .................................. 99105530
May 12, 1999 (EP) .................................. 99109503

(51) Int. Cl.
*G01N 33/53* (2006.01)

(52) U.S. Cl. ........................................................ 435/7.1

(58) Field of Classification Search .................... None
See application file for complete search history.

(56) References Cited

U.S. PATENT DOCUMENTS

| | | | |
|---|---|---|---|
| 4,898,734 A | 2/1990 | Mathiowitz et al. | |
| 5,246,715 A | 9/1993 | Orevi et al. | |
| 5,523,287 A | 6/1996 | Friedrich et al. | |
| 5,616,608 A | 4/1997 | Kinsella et al. | |
| 5,705,355 A | 1/1998 | Tolstoshev et al. | |
| 6,881,722 B1 | 4/2005 | Barnes et al. | |

FOREIGN PATENT DOCUMENTS

| WO | WO 9207005 | 4/1992 |
|---|---|---|
| WO | WO 9501375 | 1/1995 |
| WO | WO 0056885 | 9/2000 |

OTHER PUBLICATIONS

Barnes CS et al., "Production and characterization of saratin, an inhibitor of von Willebrand factor-dependent platelet adhesion to collagen," Seminars in Thrombosis and Hemostasis, vol. 27, No. 4, pp. 337-348, Aug. 2001.

*Primary Examiner*—Robert A. Wax
(74) *Attorney, Agent, or Firm*—Miller, White, Zelano, Branigan, P.C.

(57) ABSTRACT

A naturally occurring protein isolated from the saliva of the medicinal leech *Hirudo medicinalis* is described which strongly binds to collagen thus acting as an inhibitor of natural platelet adhesion to collagen. The protein has a molecular weight of about 12,000, an acidic isoelectric point and contains six cysteins. The protein was sequenced and the gene was cloned from a *H. medicinalis* cDNA-library. Procedures for producing such polypeptide by recombinant techniques are disclosed. The recombinant and the natural occurring proteins are potent inhibitors of collagen-dependent platelet adhesion and therefore useful for the therapeutic treatment of various conditions related to heart disease and diseases of the circulation system. Furthermore, the protein is useful for coating natural or artificial collagen surfaces in order to render them nonadhesive for cells and prevent the activation of cells.

6 Claims, 9 Drawing Sheets

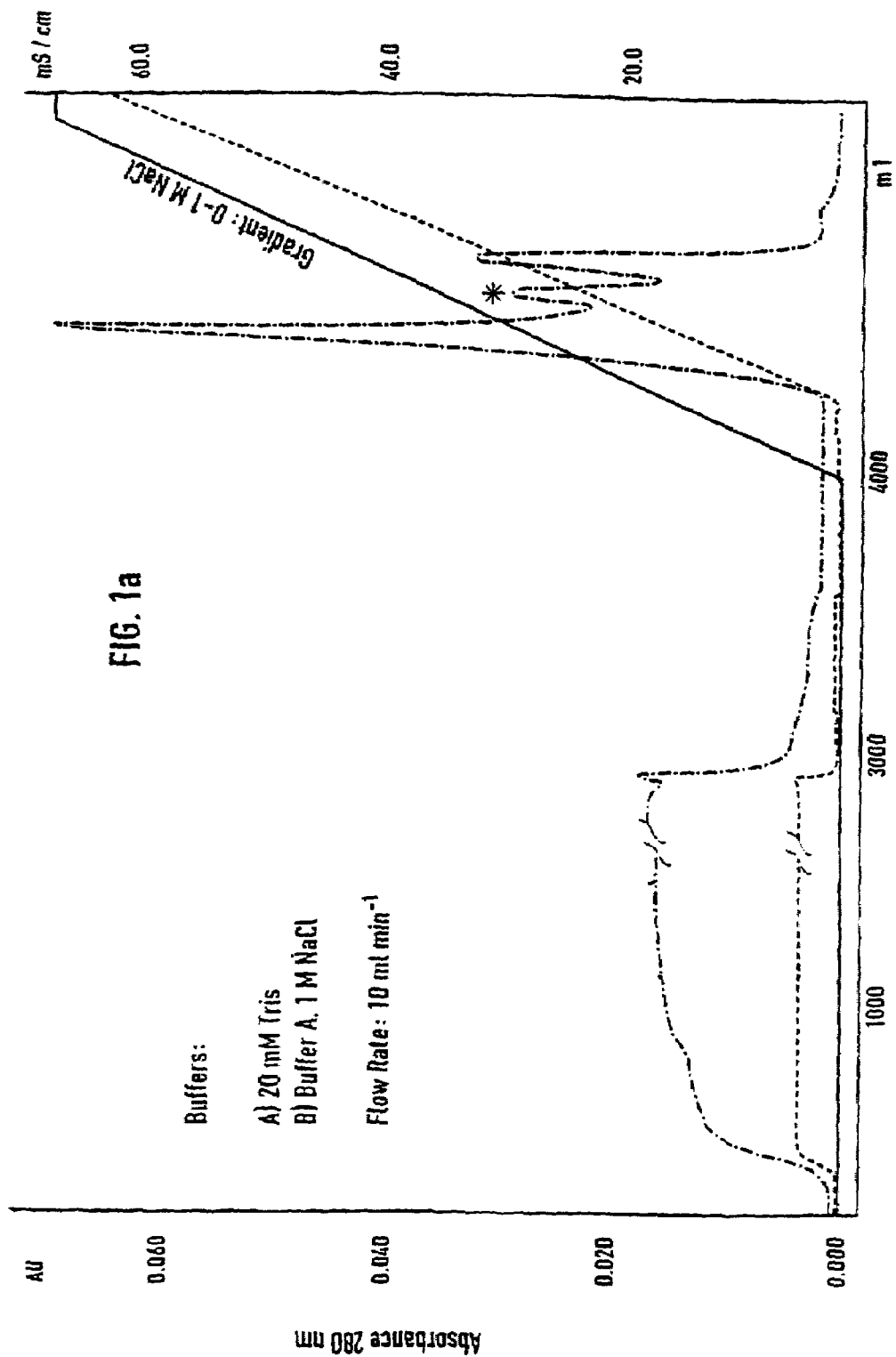

Collagen Type III from Human Placenta
Saliva # 616 0.11 mg/ml: 30 μl on coverslip n = 4
Protein # 607 0.11 mg/ml: 30 μl on coverslip n = 2

SEQUENCE LISTING

<160> NUMBER OF SEQ ID NOS: 12

<210> SEQ ID NO 1
<211> LENGTH: 375
<212> TYPE: DNA
<213> ORGANISM: Hirudo medicinalis
<220> FEATURE:
<221> NAME/KEY: CDS
<222> LOCATION: (64)..(372)

<400> SEQUENCE: 1

```
atgaagtatt tcttgatttc cttcctttgc ctcgcaagct tgctgatctc aactacttct      60 tca gaa gaa cgt gaa gat tgt tgg acg ttt tac gcg aac aga aaa tat     108
    Glu Glu Arg Glu Asp Cys Trp Thr Phe Tyr Ala Asn Arg Lys Tyr
    1               5                   10                  15 aca gac ttc gat aaa tct ttt aag aag tcc tct gat ctt gac gaa tgc     156
Thr Asp Phe Asp Lys Ser Phe Lys Lys Ser Ser Asp Leu Asp Glu Cys
             20                  25                  30 aaa aaa aca tgt ttc aag acg gag tac tgc tac atc gtt ttt gaa gac     204
Lys Lys Thr Cys Phe Lys Thr Glu Tyr Cys Tyr Ile Val Phe Glu Asp
         35                  40                  45 acg gtc aac aag gaa tgt tac tac aat gtc gtt gat ggt gaa gag tta     252
Thr Val Asn Lys Glu Cys Tyr Tyr Asn Val Val Asp Gly Glu Glu Leu
     50                  55                  60 gac caa gaa aaa ttt gtt gtc gac gaa aac ttc acg gaa aat tat ttg     300
Asp Gln Glu Lys Phe Val Val Asp Glu Asn Phe Thr Glu Asn Tyr Leu
 65                  70                  75 aca gac tgc gag ggt aaa gat gca ggt aat gcg gca ggt aca ggt gac     348
Thr Asp Cys Glu Gly Lys Asp Ala Gly Asn Ala Ala Gly Thr Gly Asp
 80                  85                  90                  95 gag tca gat gaa gtt gat gaa gat taa                                   375
Glu Ser Asp Glu Val Asp Glu Asp
                 100
```

<210> SEQ ID NO 2
<211> LENGTH: 103
<212> TYPE: PRT
<213> ORGANISM: Hirudo medicinalis

<400> SEQUENCE: 2

```
Glu Glu Arg Glu Asp Cys Trp Thr Phe Tyr Ala Asn Arg Lys Tyr Thr
 1               5                  10                  15

Asp Phe Asp Lys Ser Phe Lys Lys Ser Ser Asp Leu Asp Glu Cys Lys
             20                  25                  30

Lys Thr Cys Phe Lys Thr Glu Tyr Cys Tyr Ile Val Phe Glu Asp Thr
```

```
                      35                  40                  45
Val Asn Lys Glu Cys Tyr Tyr Asn Val Val Asp Gly Glu Glu Leu Asp
         50                  55                  60

Gln Glu Lys Phe Val Val Asp Glu Asn Phe Thr Glu Asn Tyr Leu Thr
 65                  70                  75                  80

Asp Cys Glu Gly Lys Asp Ala Gly Asn Ala Ala Gly Thr Gly Asp Glu
                 85                  90                  95

Ser Asp Glu Val Asp Glu Asp
            100

<210> SEQ ID NO 3
<211> LENGTH: 23
<212> TYPE: DNA
<213> ORGANISM: Artificial Sequence
<220> FEATURE:
<223> OTHER INFORMATION: r = a or g; m = a or c; y = c or t; and n = a
      or g or c or t
<220> FEATURE:
<223> OTHER INFORMATION: Description of Artificial Sequence:primer01

<400> SEQUENCE: 3
gargarmgng argaytgttg gac                                              23

<210> SEQ ID NO 4
<211> LENGTH: 23
<212> TYPE: DNA
<213> ORGANISM: Artificial Sequence
<220> FEATURE:
<223> OTHER INFORMATION: r = a or g; m = a or c; y = c or t; and n = a
      or g or c or t
<220> FEATURE:
<223> OTHER INFORMATION: Description of Artificial Sequence:primer02

<400> SEQUENCE: 4
gargarmgng argaytgctg gac                                              23

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:primer03

<400> SEQUENCE: 5
gcatcgatgg aagaacgtga agac                                             24

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:primer04

<400> SEQUENCE: 6
tagcgctttt gacgtcgtcg tca                                              23

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence:primer05

<400> SEQUENCE: 7
gaagaatgca aggatgagga ttattg                                           26
```

```
<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:primer06

<400> SEQUENCE: 8
aagcttctag tcttcgtcaa cttcg                                    25

<210> SEQ ID NO 9
<211> LENGTH: 94
<212> TYPE: DNA
<213> ORGANISM: Artificial Sequence
<220> FEATURE:
<223> OTHER INFORMATION: Description of Artificial Sequence:primer07

<400> SEQUENCE: 9
cggatccatg aaattcttag tcaacgttgc ccttgttttt atggtcgtat acatttctta    60
catctatgcg gaagaacgtg aagattgttg gact                              94

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:primer08

<400> SEQUENCE: 10
ggtacctcac atatcttcat caac                                      24

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:primer09

<400> SEQUENCE: 11
gcatgcggcc gcctaatctt catcaacttc                                30

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence:primer10

<400> SEQUENCE: 12
gcatgaattc gaagaacgtg aagattg                                   27
```

PROTEIN FOR BLOCKING PLATELET ADHESION

This application is a divisional of U.S. patent application Ser. No. 10/846,668 filed May 17, 2004 (U.S. Pat. No. 6,962,801), which is a continuation of U.S. patent application Ser. No. 09/936,737 filed Sep. 17, 2001 (U.S. Pat. No. 6,774,107), which claims the benefit of PCT/EP00/02117 filed Mar. 10, 2000, which are hereby incorporated by reference in their entirety.

SUMMARY OF THE INVENTION

A naturally occuring protein isolated from the saliva of the medicinal leech *Hirudo medicinalis* is described which strongly binds to collagen thus acting as an inhibitor of natural platelet adhesion to collagen. The protein has a molecular weight of about 12 000, an acidic isoelectric point and contains six cysteins. The protein was sequenced and the gene was cloned from a *H. medicinalis* cDNA-library. Procedures for producing such polypeptide by recombinant techniques are disclosed. The recombinant and the natural occuring proteins are potent inhibitors of collagen-dependent platelet adhesion and therefore useful for the therapeutic treatment of various conditions related to hard disease and diseases of the circulation system. Furthermore the protein is useful for coating natural or artificial collagen surfaces in order to render them nonadhesive for cells and prevent the activation of cells.

FIELD OF INVENTION

In haemostasis or thrombosis, platelets adhere to the cell-extracellular matrix of an injured vessel and cover the surface of the damaged area. Preventing this important initial step in the pathogenesis of thrombosis and arterial occlusion should be of therapeutic benefit in the effort of to prevent thrombotic diseases. Collagen is considered to be the most thrombogenic surface component and has been shown to be a strong stimulant for platelet adhesion, aggregation and the release of their granules leading to the recruitment of (Ruggeri, Z. M. et al.; Seminars in Hematology, 1994, 31, 229–39) additional platelets to this area to form aggregates or a thrombus. The initial contact of the platelets to the vessel surface is mediated by collagen bound von Willebrand Factor (vWF) and a specific vWF receptor on platelets, the glycoprotein Ib-V-IX complex. In addition ADP, epinephrine and circulating clotting factors drive the further activation process of platelets while simultaneously an increase in thrombin activity contributes to the formation of the cross-linked fibrin clot. Platelet-platelet aggregation supports this process and is mainly driven by fibrinogen as mediator that bridges cells through the glycoprotein IIb/IIIa receptor.

This normal physiological response is quite critical in the course of the pathological process where platelets adhere to collagenes exposend in sclerotic lesions (Van der Rest M. et al.; FASEB Journal, 1991, 5, 2814–23) and start to bild-up occlusions. Depending on the location and extent of the occlution severe complications such as myocardial infarction, stroke, inflammation or pulmonary embolism may be the severe outcome of this process.

As a direct acting antithrombotic agent heparin which blocks the thrombin activity, thus preventing the formation of fibrin rich thrombi, is the currently most well known drug used in anti-thrombotic interventions. Heparin is widely used in indications such as: unstable angina and acute myocardial infarction. However despite the wide use several severe short comings such as intravenous application, requirement for anti-thrombin-III as a cofactor, reduced affinity for clot-bound thrombin, it's inactivation by several plasma proteins, the occasional induction of thrombocytopenia and it's biological heterogeneity remain unresolved. As a consequence the results of using heparin in the clinical setting have not been overwhelming so far.

Recent development of low molecular weight heparin has contributed a version for subcutaneous application, however the therapeutic benefit over the standard heparin has been modest. Unfortunately the same applies to the other directly acting antithrombins such as Hirudin, Hirulog and Warfarin. It turned out, that one of the major problems seems to be related to the increased production of thrombin under antithrombotic treatment (Rao, A. K et al., Circulation, 1996, 94, 389–2395).

Other recent strategies have therefore been focussed to the process of prothrombin activation which is driven by Factor Xa. The major challenge is the design of appropriate inhibitors directed to this factor. In summary on would therefore argue that the full therapeutic potential of this type of intervention has not yet been realized.

Another pannel of therapeutics is represented by the thrombolytic regimens and has been focussed on the development of staphylokinase, streptokinase, urokinase type Plasminogen Activator, tissue type Plasminogen Activator and anisoylated-plasminogen-streptokinase activator complex. The differences in time necessary to inducing reperfusion is remarkable different for each of these thrombolytic agents, however the contribution in terms of reducing the overall mortality is equal for all the products. In addition reocclusion or prolonged bleeding are frequent complications. This might be due to relatively low specificity for fibrin and the short plasma half-life of these compounds. Currently various application regimens and combinations of different fibrinolytic principles are tested in order to overcome some of the current short comings in thrombolytic therapie. The improvement which are expected are however rather small.

Recently a new group of patients occured with probelms such as acute thrombotic occlusion and late restenosis due to procedures such as angioplasty, atherectomy, arterial grafting or vessel wall stenting. The possible therapeutic interventions comprise anti-platelet, antithrombotic and thrombolytic strategies. Various other agents such as ticlopdine acting as ADP antagonists or Calcium ionophore A-23187 and especially Asprin have a direct influence on the platelet function and have been suggested or used to prevent or minimize platelet aggregation. The new anti-platelet adhesion substance according to this invention could as well help to overcome these clinical complications when applied during surgery.

Another complication related to this topic arises if artificial surfaces come in contact with blood, then their is increased tendency to induce thrombotic events by activation of platelets and/or induction of coagulation. These effects may cause failure of vascular grafts, cardiac valves, stents, catheters or any other blood contacting device or material. The ability of the protein disclosed here to create non-thrombogenic surfaces may therefore be further exploited by immobilization of this protein to the materials and devices described above. Such a treatment should render such materials or devices biocompatible and thromboresistant.

Due to the limitations associated with the available antithrombotic agents there is an actual need for new alternative strategies and therapeutics.

BACKGROUND OF THE INVENTION

A potential for future improvements in the treatement of caridvacular disorders may be contributed by approaches as disclosed in this invention which directely interfere with the collagen and/or vWF factor induced platelet adhesion.

Several novel inhibitors which prevent platelet adhesion are monoclonal antibodies directed to vWF. It has as well been suggested that glycoprotein IIb/IIIa inhibitors may be beneficial in inhibiting platelet adhesion Some of these inhibitors like the monoclonal Ab c7E3 have already been tested clinically while others like the KGD- and RGDF-inhibitors are still under study. However, the specificity of most of these new inhibitors is not very well studied thus the spectrum of side effects that will be induced by using this inhibitors is still open and deserves carefull examination.

A rich source for the screening of new compounds that interfere with collagen induced platelet adhesion is given in nature through blood-sucking animals. Several inhibitors have been isolated from nature as described in the literature: A 65 kD protein called Calin isolated from *Hirudo medicinalis* (U.S. Pat. No. 5,587,360, WO 92/07005) (Munro, R., et al., Blood Coagulation and Fibrinolysis, 1991, 2, 179–184) and a 16 kD (LAPP) protein isolated from the salivary glands of the leech *Haementeria officinalis* (U.S. Pat. No. 5,324,715). Both proteins have been described as aggregation inhibitors as tested in static assays of collagen dependent platelet aggregation.

Despite a proven in vitro activity LAPP failed to act in several well-established in vivo models (Schaffer L. W. et al.; Arterioscler. Thromb., 1993, 13, 1593–1601) and Connolly T. M. et al.; Thromb. Haemostas., 1993, 69, 589). The soft tick, *Ornithodoros moubata*, also contains an antiplatelet protein (Moubatin) which is active in preventing collagen-stimulated platelet aggregation (Waxman, L. et al.; J. Biol. Chem., 1993, 268, 5445–49). Another inhibitor of platelet aggregation from a blood-sucking bug was disclosed in WO 9309137 by Noeske-Jungblut C. et al. Smith et al. have isolated a 50 kDa protein from snake venom and a 19 kDa protein was isolated from a the saliva of *Triatoma pallidipennis*, a blood-sucking bug. The protein was found to contain a factor that specifically inhibits collagen-induced platelet aggregation. The 19 kDa protein named pallidipin inhibits collagen-mediated aggregation of platelets in plasma. No inhibition of aggregation stimulated by other effectors (ADP, thrombin, thromboxane A2 mimetic U46619, phorbol ester) was detected. Pallidipin had no effect on platelet adhesion to collagen but inhibited ATP release from platelets. It interacted reversibly with platelets and may share with collagen a common target on them. The precise mechanism of action and therapeutic benefit of this protein is under investigation. Gan et al. described Echistatin as an inhibitor binding to the fibrinogen receptor GP IIa/IIIb (J. Biol. Chem. 1988, 263, 19827–32).

Despite these exciting developments, the need continues to exist for supplying further anticoagulants and antithrombin which have increased efficacy in the inhibition of clot formation, vWF-induced platelet activation or endothelial cell activation and which may be used pharmaceutically and produced in commercially feasible quantities.

Since none of the known proteins described so far has developed into a compound with ideal therapeutic profile the inventors of the present invention decided to go ahead with a new screening strategy in order to detect more relevant proteins.

DESCRIPTION OF THE INVENTION

In this invention an inhibitor isolated from *H. medicinalis* is described which directly acts one collagen-platelet interaction thus inhibiting platelet activation and early platelet— platelet interaction.

So far, there has not been a positive example in the literature, which indicates that by using a screening approach that would exclude aggregation inhibitors as well as lytic proteins from a source of naturally occurring compounds one could identify new anti-adhesive mechanisms or compounds. However this strategy was used in this invention. Since at least six different platelet surface glycoproteins are known to be involved in collagen adhesion and in addition several platelet derived compounds such as von Willebrand factor, fibronectin and thrombospondin have been shown to be involved as indirect mediators of collagen-platelet adhesion there has been little optimism in the beginning to identify a new adhesion inhibitor.

Nevertheless, this approach was used to screen *Hirudo medicinalis* saliva knowing that not all the documented or unkown vWF related inhibitors as well as compounds directely acting on platelet receptors could be excluded. Thus the result of the screening was a surprise: A new protein named Saratin with anti-adhesive activity for platelet which can be isolated from tissues and secretions of well investigated leech of the species *H. medicinalis*.

The present invention comprises the active polypeptide Saratin isolated from the leech *H. medicinalis*. The protein was isolated from saliva by a combination of pressurized dialysis and at least one chromatographic step like anionic exchange chromatography and at least one reversed phase high performance chromatography (RP-HPLC) step. The pressure dialysis step turned out to be absolutely critical during the recovery of Saratin from saliva, since the strong concentration of saliva helped to overcome the otherwise tremendous loss of bioactive Saratin. The isolated Saratin binds strongly to several collagens and blocks the adhesion of platelets to collagen coated such surfaces in a dose dependent fashion.

In order to optimize the screening cascade currently available techniques have been developed to distinguish platelet adhesion and platelet aggregation: the ability of platelets to retard or stop flow through fibers, the contribution of platelets to in vitro clot formation, glass bead adhesion laboratories, or whole blood flows through the filter and platelet adhesion of anticoagulated platelet-rich plasma to filters composed of glass fibers or collagen under a regulated pressure gradient.

The protein (named Saratin) is characterized by the amino acid sequences depicted in sequence (SEQ. ID. NO. 2) and is constituted from 103 amino acids which make up a theorectical relative molecular weight of approximately 12068 dalton∓1 kDa The protein exhibits a unique primary structure with no significant similarity to other previously described sequences. The protein is rich in aspartic and glutamic acid which contributes to the low isoelectric point of pH 3.7∓0.5 of the molecule as measured by IEF-PAGE.

SDS-PAGE analysis demonstrated a strong shift in mobility upon reduction of the protein proir to electrophoresis, indicating posttranslational modifications. Sequencing of the polypeptide had revealed six cysteine molecules which could make-up post-translational modifications of the protein. Electrospray mass spectrometry of Saratin revealed an actual molecular weight of 12061 indicating that up to three disulphide bonds are involved in the formation of the secondary structure of the native form of the protein.

The adhesion inhibitor according to the present invention is new because it differs from known aggregation inhibitors isolated from leeches especially from Calin or LAPP in the molecular weight, isoelectric point and amino acid sequence and biological activities.

The present invention provides as well isolated DNA comprising a polynucleotide encoding the leech derived platelet adhesion inhibitor having the amino acid sequence as shown for the protein. The nucleotide sequence representing the cDNA clone is shown in SEQ. ID. NO. 1, Position 1–63 of the nucleotide sequence represents a putative 21 amino acid leader sequence and position 64–372 contains an open reading frame coding for a polypeptide of 103 amino acid residues and an amino acid sequence as shown for the mature protein in SEQ. ID. NO. 2.

The present invention also relates to recombinant vectors which include the synthetic gene coding for the leech-derived platelet adhesion inhibitor of the present invention, and a host cell containing the recombinant vectors. Methods for recovering and isolating the expressed proteins have been based on tag-technologies or have been adapted from the purification scheme developed for the naturally occuring Saratin. Depending on the individual protocols used for extracellular or intracellular expression in yeast cells, insect cells, baby hamster kidney cells and *E. coli* cells transformed with the appropriate vectors the steps for recovering the recombinant protein from the supernatant or sediments have to be adapted by techniques known to the expert. Excellent expression was found in *E. coli* as a host, where periplasmatic expression was contributed by insertion of a pelB leader sequence. Products recovery from *Escherichia coli* (*E. coli*) was achieved (arround 5 mg/l) after osmolysis and centrifugation. *Saccharomyces cerevisiae* (*S. cerevisiae*) (>10 mg/l culture broth) with the alternative yeast adopted vector was used in a paralelled experiment. The secreted material was isolated by centrifugation. Purification was achieved by cross-flow filtration and ion exchange chromatography. In other expression approches using either COS cells or CHO cells product expression was arround 750 ng/ml. The purified recombinant material proved to be pure and homogeneous by electrophoretic and chromatographic analysis and identical to saliva derived Saratin as demonstrated by amino acid sequencing and molecular mass determination.

The invention also comprises methods for purifying the active protein from crude saliva of the leech and measuring its activity against platelets by static and dynamic assay methods as well as the use of this method to isolate rekombinant protein.

Techniques for the production of Saratin, include the Examples 6, 7, 8 and 13 however the expression methods to be used are not restricted to these examples. For instance transgenic mice, or other organisms, including other mammals, may as well be used to express Saratin.

Proteins of the present invention include variants which conserve the activity of the disclosed sequences, including fragments or subunits, naturally occuring variants, allelic variants, randomly generated artificial mutants and intentional sequence variations such as adding which conserve activity. Fragments or subunits refers to to any portion of the sequence which contain fewer amino acids than the complete protein e.g. partial sequences excluding portions of the N- and/or C-termini of the complete protein.

The invention further covers hybrid proteins, such as fusion proteins or proteins resulting from the expression of multiple genes within the expression vector, and may include a polypeptide having the specific activity of a disclosed protein linked by peptide bonds to a second polypeptide. Notably other variants of the proteins of the present invention are included, especially any variants that differ from the isolated protein only by conservative amino acid substitution. Such conservative amino acid substitutions are defined in Taylor et al., J. Mol. Biol., 1986, 188, 233.

Also included are methods for using the proteins to prevent or delay of platelet activation by inhibition of collagen-platelet interactions. The protein is useful in the prevention, prophylaxis, therapy and treatment of thrombotic diseases. Unlike all these previously described proteins, which act at various surface proteins on the platelet, the protein from this invention has a unique mechanism of action. It binds tightly to the collagen surface and one mechanism of action is given by the coverage of specific collagen sides no longer available for interactions and binding of platelets. This type of new mechanism has the great advantage, that the platelets stay functionally intact during the application of the protein, so that very low or even no bleeding tendency is expected from this treatment.

Another important area of use is the treatment of various surfaces with the protein to render them non-adhesive for platelets and thereby create blood-compatible devices.

As indicated above, the polypeptides according to the present invention are suitable as pharmaceutically effective compounds in parmaceutical compositions and combinations.

The pharmaceutical formulations according to the invention optionally may comprise additional active incredients like Aspirin, anti-coagulants such as hirudin or heparin or thrombolytic agents such as plasminogen activator or streptokinase.

The novel polypeptide according to the invention may form pharmaceutically acceptable salts with any non-toxic, organic or inorganic acid. Inorganic acids are, for example, hydrochloric, hydrobromic, sulphuric or phosphoric acid and acid metal salts such as sodium monohydrogen orthophosphate and potassium hydrogen sulfate. Examples for organic acids are the mono, di and tri carboxylic acids such as acetic, glycolic, lactic, pyruvic, malonic, succinic, glutaric, fumaric, malic, tartaric, citric, ascorbic, maleic hydroxymaleic, benzoic, hydroxybenzoic, phenylacetic, cinnamic, salicylic and sulfonic acids such as methane sulfonic acid. Salts of the carboxy terminal amino acid moiety include the non-toxic carboxylic acid salts formed with any suitable inorganic or organic bases. These salts include, for example, alkali metals such as sodium and potassium, alkaline earth metals such as calcium and magnesium, light metals of Group IIIA including aluminium, and organic primary, secondary and tertiary amines such as trialkylamines, including triethylamine, procaine, dibenzylamine, 1-ethenamine, N,N'-dibenzylethylene-diamine, dihydroabietylamine and N-alkylpiperidine.

As used herein, the term "pharmaceutically acceptable carrier" means an inert, non toxic solid or liquid filler, diluent or encapsulating material, not reacting adversely with the active compound or with the patient. Suitable, preferrably liquid carriers are well known in the art such as steril water, saline, aqueous dextrose, sugar solutions, ethanol, glycols and oils, including those of petroleum, animal, vegetable, or synthetic origin, for example, peanut oil, soybean oil and mineral oil.

The formulations according to the invention may be administered as unit doses containing conventional nontoxic pharmaceutically acceptable carriers, diluents, adjuvants and vehicles which are typical for parenteral administration.

The term "parenteral" includes herein subcutaneous, intravenous, intra-articular and intratracheal injection and infusion techniques. Also other administrations such as oral administration and topical application are suitable. Parenteral compositions and combinations are most preferably adminstered intravenously either in a bolus form or as a constant fusion according to known procedures.

Tablets and capsules for oral administration contain conventional excipients such as binding agents, fillers, diluents, tableting agents, lubricants, disintegrants, and wetting agents. The tablets may be coated according to methods well known in the art.

Oral liquid preparations may be in the form of aqueous or oily suspensions, solutions, emulsions syrups or elixirs, or may be presented as a dry product for reconstitution with water or another suitable vehicle before use. Such liquid preparations may contain conventional additives like suspending agents, emulsifying agents, non-aqueous vehicles and preservatives.

Topical applications may be in the form of aqueous or oily suspensions, solutions, emulsions, jellies or preferably emulsion ointments.

Unit doses according to the invention may contain daily required amounts of the protein according to the invention, or sub-multiples thereof to make up the desired dose. The optimum therapeutically acceptable dosage and dose rate for a given patient (mammals, including humans) depends on a variety of factors such as the activity of the specific active material employed, the age, body weight, general health, sex, diet, time and route of administration, rate of clearance, the object of the treatment, i.e., therapy or prophylaxis and the nature of the thrombotic disease to be treated, antiplatelet or anticoagulant activity.

Therefore, in compositions and combinations useful as antithrombotic in a treated patient (in vivo) a pharmaceutical effective daily dose of the peptides of this invention is between about 0.01 and 100 mg/kg body weight, preferably between 0.1 and 10 mg/kg body weight According to the application form one single dose may contain between 0.5 and 10 mg. of the thrombin inhibitor To achieve an anticoagulant effect in extracorporeal blood a pharmaceutically effective amount of the inventive peptides is between 0.2 and 150 mg/l, preferably between 1 mg and 20 mg/l extracorporeal blood.

It is also object of this invention to provide an implantable or extracorporal medical device for use in contact with body fluids in order to render the device surface substantially thromboresistant, coated with an immobilized polypeptide as defined above and in the claims. The polypeptide according to the invention is immobilzed on a medical device so as to render the surface biocompatible and thromboresistant. Such devices sometimes have surfaces properties which typically induce platelet aggregation, which is a disadvantage in their intended uses in inplantable and extracorporeal devices in contact with blood or other body fluids. Examples for such devices which are commonly made from plastics materials and synthetic fibres are protheses, artificial organs, ocular lenses, sutures, artificial vascular segments, catheters, dialysers, tubes and vessels carrying blood.

Posterior capsule opacification (PCO) is a common complication after cateract extraxtion, despite the modern surgical techinques and lenses which are used for this procedure. PCO is caused by the proliferation and migration of lens epithelial cells across the posterior capsule thus reducing the visual acuity. Physical treatments as well as chemically modified lenses have been proposed to reduce formation of PCO. Heparin lens coating or topical heparin eyedrops have been used to reduce PCO, indicating that thrombogenic mechanisms are involved in the formation of PCO.

Saratin has been shown to have significant advantages over heparin in preventing and blocking thrombogenicity. It is therefore another feature of this invention to provide a coating comprising Saratin which reduces thrombogenicity of the lens material used for refractive anterior or posterior chamber ocular implants which may be surgically implanted into the eye. This new type of coating avoids problems contributed by stimulated cell growth. In combination with other medicaments which are for instance confering cell death, Saratin coating-helps to completely overcome posterior capsule opacification.

BRIEF DESCRIPTION OF THE FIGURES

Details of the figures are explained in examples 1 to 10.

DETAILED DESCRIPTION OF THE INVENTION

Example 1

Screening Adhesion Inhibitors

Platelet adhesion to collagen has been the functional background four screening saliva components. In addition four additional tests available for the assesment of various actions of antithrombotic drugs such as the AZOCOLL assay, amidase activity assay, vWillebrand dependent binding assay and platelet aggregation assay have been used to exclude functional properties which idealy would not be linked to an adhesion inhibitor. While most of this assays used here are standard assays, the platelet adhesion assay had to be modified to fitt our specific needs. In short: Horm collagen (Nycomed) has been coated to 96 well plates (Nunc) by using acidified collagen at a concentration of 20 µg/ml and incubating the plates overnight. After washing the plates 3 times with PBS the residual surface of the wells have been blocked with 1% BSA. Platelets isolated freshly from human citronylated blood have been added simultaneously with fractions derived from the individual column steps. When required pre-activation of platelets has been performed by incubating platelets prior to use in TBS in the precence of bivalent magnesia ions. Raw saliva, standardized to a total protein concentration of 200 µg/ml, has been used as a standard to compare for inhibitory activity. The platelet inhibition assay turned out to be highly susceptible to buffer changes and elevated salt concentrations. Since all the samples have been processed by ion-exchanger chromatography the direct testing of the fractions in the inhibition assay turned out to be complicated and unreliable. Therefore all samples to be tested have been applied to a Centricon based concentration step which simultaneously reduced ionic strenght and supports concentration prior to measurement.

Example 2

Purification of a Natural Inhibitor

The invention used saliva collected from *H. medicinalis* which is known to contain a number of bioactive proteins such as hirudin, elastase inhibitors, collagenases and platelet aggregation inhibitors such as calin (Munro, R. et al.; Blood Coagulation and Fibrinolysis, 1991, 2, 179–184) and LAPP (Schaffer, L. W. et al.; Arterioscler. Thromb., 1993, 13, 1593–1601). Besides this characterized proteins the majority of the roughly eighty proteins detectable by SDS-PAGE are still unkown. In the present invention the fractionated saliva and the screening strategy as described in Example 1 was used in order to screen for the novel proteins that interferes directly with platelet collagen interaction.

Figure 1B:
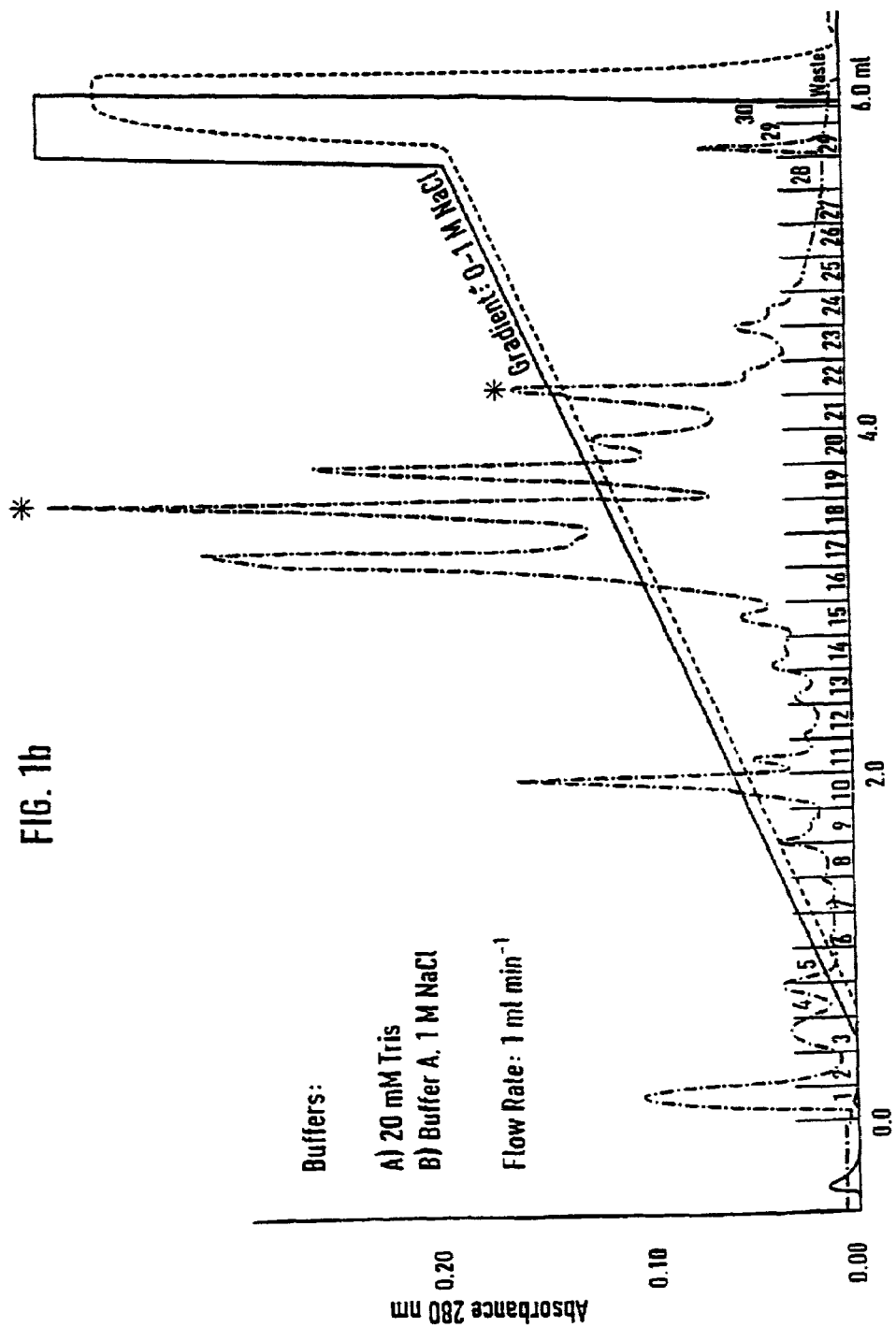
FIG. 1
Separation of saliva components. Elution of Saratin is marked by∗
a) shows the separation profile of saliva after DEAE anion exchange. Saratin fractions have been collected from peak 3 (Example 2).
b) shows re-chromatography of pooled fractions on Mono Q HR5/5. Samples have been collected from the last part of the major peak as indicates by bar (Example 2).
c) shows last chromatography step on semi-preparative analytical RP-HPLC of Saratin positive fractions collected from Mono Q HR5/5 (example 2). Active Saratin was recovered from the major peak (peak 3).
Figure 1C:
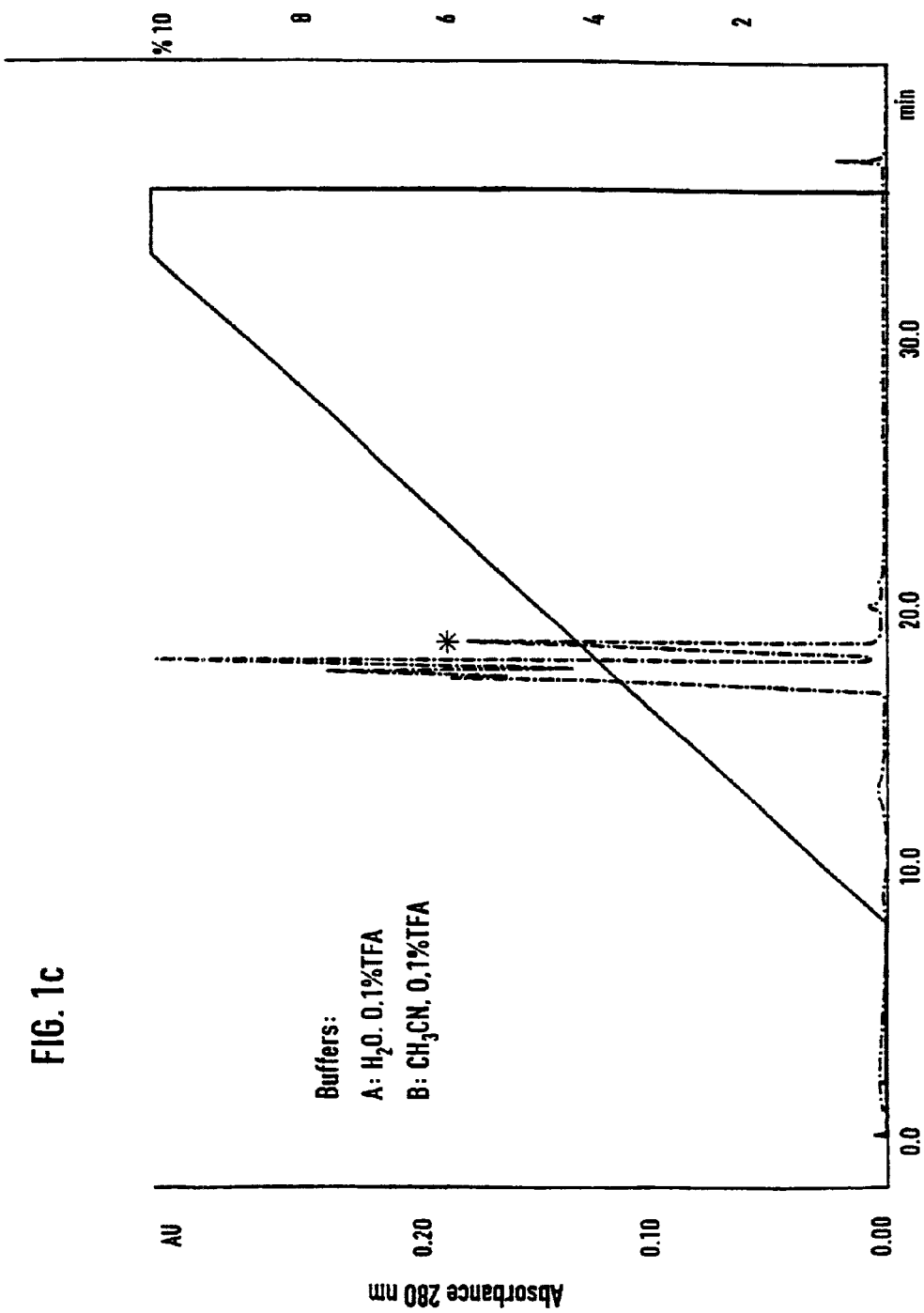
Figure 2:
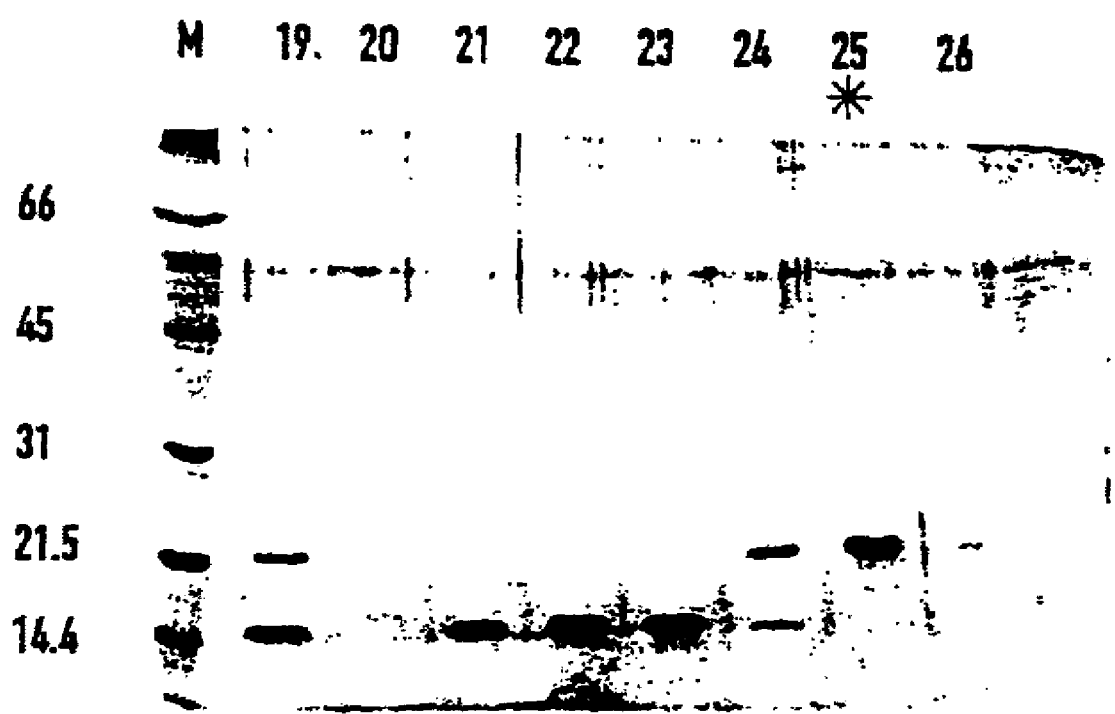
FIG. 2
SDS-PAGE of fractions collected from RP-HPLC. Saratin positive fractions are marked ∗(Examples 2 and 3).
Figure 3:
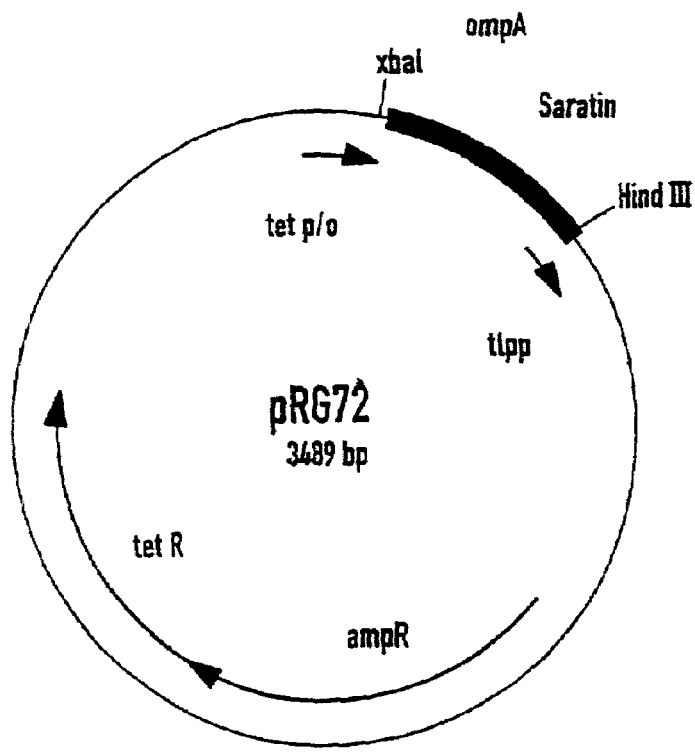
FIG. 3
E. coli expression vector for Saratin (Example 7).

Separation of an adhesion inhibitor activity from raw saliva turned out to be a critical task, mainly due to the irreversible loss of most of the adhesion inhibitory activity in the first chromatographic step. Additives such as 12% ethanol and divalent cations as recommended by Munro, R. et al did not improve the situation. However the high salt concentration of the saliva in combination with the low overall protein concentration (190–250 µg/ml) asked for an initial concentration or buffer exchange step. Thus several strategies for enrichment, concentration or buffer exchange were explored. Traditional dialysis led to the complete loss of activity. Most of the other standard techniques such as ion exchangers, affinity columns, size exclusion (loss was irrespective of the column resin) failed independent of the nature of the separation technology or buffer and addditives used. Surprisingly it turned out, that pressurized dialysis of 500 ml saliva was a successful method to concentrate the saliva proteins (about 30–40 times) and simultaneously get ride of the unwanted buffer components. Unexpectedly the saliva raw material processed in this way was an ideal starting material for further purification and the recovery of bioactivity anti-adhesive components out of the saliva was no longer a real problem. Since cation exchangers or affinity colums turned out ot be an insufficient step in purification, weak anion exchanger such as DEAE-Fastflow or EMD-DEAE-Fractogel were used. 12% ethanol and divalent cations have been tested, however the results were similar with or without this additives. Further optimization of the chromatographic steps led to a sequence of DEAE-column, Mono Q-column and as a final step an reversed phase RP18 column. Optimization of the chromatographic conditions have been performed on a BiaCore chromatographic system using analytical columns available from Pharmacia. The gradients used to operate the DEAE-column, Mono Q-column and RP18 colums are given in FIGS. 1*a, b, c*. The BiaCore based separation has been scaled up by using FPLC techniques. The optimized running conditions have been directly converted into the a semi-preparative scale of separation by following the instruction of the manufacturer with the exception of the RP18 column step which was maintained with Biacore technique in order to minimize loss of purified material. Recovery of purified protein from the last chromatographic RP-step was done by speed vaccuum centrifugation. Samples collected from the last RP-step have been collected and analysed by SDS-PAGE (FIG. 2) Subsequently samples have been resuspended in PBS and used to perform analytical as well as functional tests. Typically a yield of about 750 µg/l Saratin was recovered from unprocessed saliva.

Example 3

Biochemical Characterization

Purification of Saratin as disclosed in Example 1 led to an essentially pure protein with an apparent moleculare weight around 21 kDa shown under reducing conditions in SDS-PAGE (FIG. 2) The complete amino acid sequence was obtained by direct sequencing of the first 48 amino acids of the purified protein and was completed by the sequencing of several internal peptides generated via enzymatic degradation. The complete protein sequence is disclosed in SEQ. ID. NO. 2

The protein is composed of 103 amino acids with an calculated molecular weight of 12067.9 and an actual molecular weight of 12061.9 as deduced by ESI-Mass spectrometry. This differences in theroretical and measured molecular weight indicates that all the six cysteins identified in Saratin are involved in the formation of S—S bridges. This finding is supported by the observation of a strong change in mobility of the protein when chromatographed in SDS-PAGE under reducing or none reducing conditions. Futhermore the protein is rich in acidic acids such as Glu and Asp. Isoelectric focussing using IEF-PAGE (Immobiline) technique revealed an isolelectric point of pH 3.7∓0.5. In a comparative study we have used the purified leech protein as a reference and compared it with the physicochemical properties of recombinat Saratin derived from baculo, yeast and *E. coli* expression. All three protein turned out to be identical in their properties. Characterization of protein by SDS-PAGE visualized by Coomassie (FIG. 2) or silver-staining and/or Western blot analysis revealed, that the protein was homogeneous and in a none glycosylated form.

Example 4 mRNA Preparation and cDNA Synthesis

RNA was prepared from the medicinal leech, *Hirudo medicinalis*; using guanidinium thiocynate method. mRNA was purified from total RNA using "Oligotex mRNA kit" (QIAGEN).

cDNA was synthesized using "Marathon cDNA Amplification kit" (CLONTECH). The DNA sequence encoding Saratin was initially amplified using PCR oligonucletide primers according to the instruction of the supplier. After cDNA synthesis, a universal adaptor was ligated to both ends of the cDNA. The sequences of the universal adaptor and the universal primers AP1 or AP2 was chosen according to the instructions of the supplier of said kit.

Example 5

Amplification and Isolation of the Saratin Gene by PCR

Degenerate primers have been synthesised based on the immediate N-terminus of the reverse translated Saratin amino acid sequence.

These primer01 and primer02 have been designed to hybridize specifically to the 5'-end of the Saratin cDNA. The primer design was based on the reverse translated amino acid sequence of the experimentaly determined eight N-terminal amino acids of the purified Saratin protein. The two primers primer01 and primer02 were synthsized to keep the degeneracy as low as possible and to give the primers at the critical 3'-end a stretch of 8 basepairs of perfect match with the Saratin cDNA sequence in order to ensure efficient and specific amlification of the template cDNA. According to the DNA degenerate alphabet (IUPAC code) R=A or G; M=A or C; Y=C or T; and N=A or G or C or T.

A 3'-RACE PCR reaction was carried out using a mixture of the primer01 and primer02 and one universal primer AP1 or AP2. PCR products were cloned in TA cloning vector pCR2.1 or pCR Script SK(+) vector and sequenced. After sequencing several of the 3'-RACE PCR fragments obtained, the Saratin gene sequence was obtained, with the exeption of the 5'-untranslated region, the signal peptide sequence and the sequence coding for the first 8 amino acids from the N-terminus of the mature protein. In order to obtain this missing Saratin cDNA sequence information, a 5'-RACE experiment was performed using a gene specific primer from the middle of the Saratin cDNA and one of the universal primers AP1 or AP2. After sequencing several of the resulting 5'-RACE PCR fragments, the complete Saratin gene sequence was obtained. Amplifying the Saratin gene by PCR using gene specific, non-degenerate primers from both the 3'-end and the 5'-end of the Saratin gene, a full length of Saratin gene was obtained.

DNA Sequencing was performed with more then 15 different PCR clones. However only one significant change which caused amino acid sequence change in only one clone was found. It is very likely that this change was caused by PCR. Another five silent changes which do not cause amino acid sequence change were found. Thus it is unlikely that these changes were caused by PCR, because the same changes were found in different clones.

The Saratin gene ORF is 372 bp and contains a 21 amino acid signal sequence and a 103 amino acid sequence coding for the mature protein. The amino acid sequence deduced from the PCR clone was found to be identical to the sequence obtained by sequencing of the natural saliva derived protein.

Example 6

Expression in COS Cells and the Detection of Expressed Protein

In order to express Saratin gene in mammalian cells such as COS or CHO, Saratin gene was cut from the vector pCR Script SK(+) using XhoI+XbaI and cloned into mammalian cell expression vector pCI-neo (Promega). pCI-neo was chosen because it contains T7 and T3 promoter for in vitro expression and neomycin resistant gene for G418 selection, and can be used in both COS and CHO cells.

In addition to the signal sequence and mature protein sequence, the insert contains a Koz sequence at the 5'-end for efficient translation and the his-tag MRGS$(H)_6$ at the 3'-end (C-Terminal) for detection of protein expression, purification and concentration. The plasmid constructure was named pNC-31.

pNC-31 plasmid DNA was used for the transfection of COS cells. The COS cells growing at log phase were washed twice with PBS and dissolved in PBS at a concentration of $1\times10^7$/ml. Then 12 μg plasmid DNA (less than 50 μl in $H_2O$ or TE buffer) was added in 0.7–0.8 ml COS cells suspension and mixed in a electroporation cuvette. Electroporation was performed at 1.9 kv, 25 μFD for 10 min and transfered to a 90 mm plate. After adding 8 ml DMEM medium containing 10% FCS and antibiotics the cells were grown for three days. The supernatantes and the cells have been used for further isolation of protein and detection. The expressed protein was detected by western blotting method using anti-MRGS(H)6 antibody. Purification was performed using chelators such as NTA or imido acetic acid immobilized on a column matrix and modified with metall ions such as Co, Ni, or Cu.

Example 7

Construction of the *E. coli* Expression Vector and Expression

Because of the variable codon usage in different biological systems, some codons are used very rarely in *E. coli*. In order to enable expression an optimized version in *E. coli* the gene had to be converted to *E. coli* codon usage according to standard procedures.

The expression in *E. coli* was performed using a modified version of the plasmid pASK75, which carries the tet promoter region. (Skerra, A., et al. Gene, 1994, 151, 131–135). In short: The modification was made by cloning a new linker between the XbaI and the Hind III sites (FIG. 3). The new linker contains the ompA leader sequence, another multiple cloning site and a 6×His-tag instead of the strep-tag.

To construct the expression vector for Saratin it was necessary to introduce 5' Cla I and 3' Eco47III restriction sites by PCR method.

Therefore the 5'-primer03 and the 3' primer04 have used. The PCR product first was cloned into the PCR II vector system (Invitrogen) and sequenced.

In a second step the Saratin gene was cloned into the modified pASK75 vector using the rectriction sites 5' ClaI and 3' HindIII.

After expressing and proving the activity of this recombinant Saratin in a second PCR reaction the His-tag was removed and the start codon of the Saratin gene was directly fused to the omp A leader sequence. The 5'-primer05 and the 3' primer06 for this PCR reaction are given in the sequence listing.

As an example for the expression in *E. coli* the expression vector pRG72 (FIG. 3), which contains the structural gene of Saratin fused to the ompA leader sequence, was transformed into W3110 competent cells. Cells have been induced after they have been grown to mid-log phase. 1 hour thereafter the recombinant Sarastatin could be clearly detected.

Example 8

Construction of the Baculo Donor Plasmid and Expression

Figure 4:
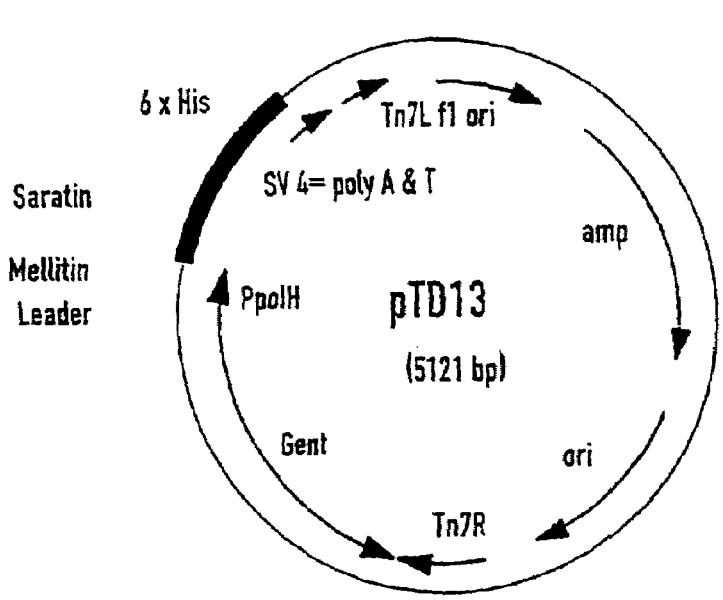
FIG. 4
Baculo donor plasmid for Saratin (Example 8)
FIG. 5
Whole blood has been exposed to an artifical collagen surface and platelets adhesion has been visualized by staining. Saratin has been used as an inhibitor (Protein #607) Example 9
FIG. 6
Inhibition of platelet adhesion on collagen type III coated coverslips under shere conditions. Comparison of saliva and saratin. Example 9
FIG. 7
Saratin exhibits dose dependent inhibition of platelet binding adhesion to collagen type III coated coverslips under shere conditions. Example 9
FIG. 8
Yeast expression vector for Saratin (Example 13)

For expression of Saratin in the Baculo virus expression system the Bac-To-Bac™ Baculovirus Expression System from Gibco Life Technologies was used. To get a selection system the Honeybee melitin leader sequence was fused to the Saratin gene and to introduce the restriction sites 5' BamHI and 3' KpnI one single PCR reaction was carried out using the 5'-primer07 and the 3'-primer08. The corrresponding PCR product was cloned into the PCR II Vector (Invitrogen) and sequenced. Then the Melitin-Saratin fusion was cloned into the pFastBac vector using the restriction sites 5=BamHI and 3'KpnI resulting in pTD13 (FIG. 4). Generation of recombinant baculoviruses and Saratin expression was performed with the Bac-To-Bac Expression System. The donor plasmid pTD13 was transformed into DH10Bac competent cells which contain the bacmid with a mini-attTn7 target site and the helper plasmid. The mini-Tn7 element on the donor plasmid ca transpose to the a mini-attTn7 target site on the bacmid in the presence of transposition proteins provided by the helper plasmid. Colonies containing recombinant bacmids were identified by disruption of the lacZ gene. High molecular weight mini-prep DNA is prepared from selected *E. coli* clones containing the recombinant bacmid, and this DNA was then used to transfect insect cells. Detailed descriptions are included in the instruction manual of the expression kit.

Example 9

Platelet Adhesion to Collagen Under Flow Conditions (Dynamic Assay)

In the platelet adhesion assay, whole human blood is perfused through a parallel flow chamber to examine the adhesive activity of platelets to a collagen coated coverslips under high shear flow (simulating in vivo arterial conditions) as originally described by Sakariassen et al (Meth. Enz., 1988, 169, 37–70). Human placental collagen, type III (Sigma), solubilized in 50 mmol/L acetic acid was sprayed onto cleaned glass coverslips (18 mm×18 mm) with a retouching airbrush. Coverslips were stored in PBS at 4° C. overnight.

Fresh whole human blood (anticoagulated with low molecular weight heparin; 20 U/ml) was prewarmed at 37° C. for 10 min before being used. Preparations of proteins according to this invention were pipetted onto coverslips (30 µl per coverslip) and incubated for 10 min in a humid chamber at room temperature before being inserted into the perfusion chamber. The blood was allowed to perfuse through the chamber (at 37° C. for 5 min at a shear rate of 1300 $s^{-1}$.)

Figure 5:
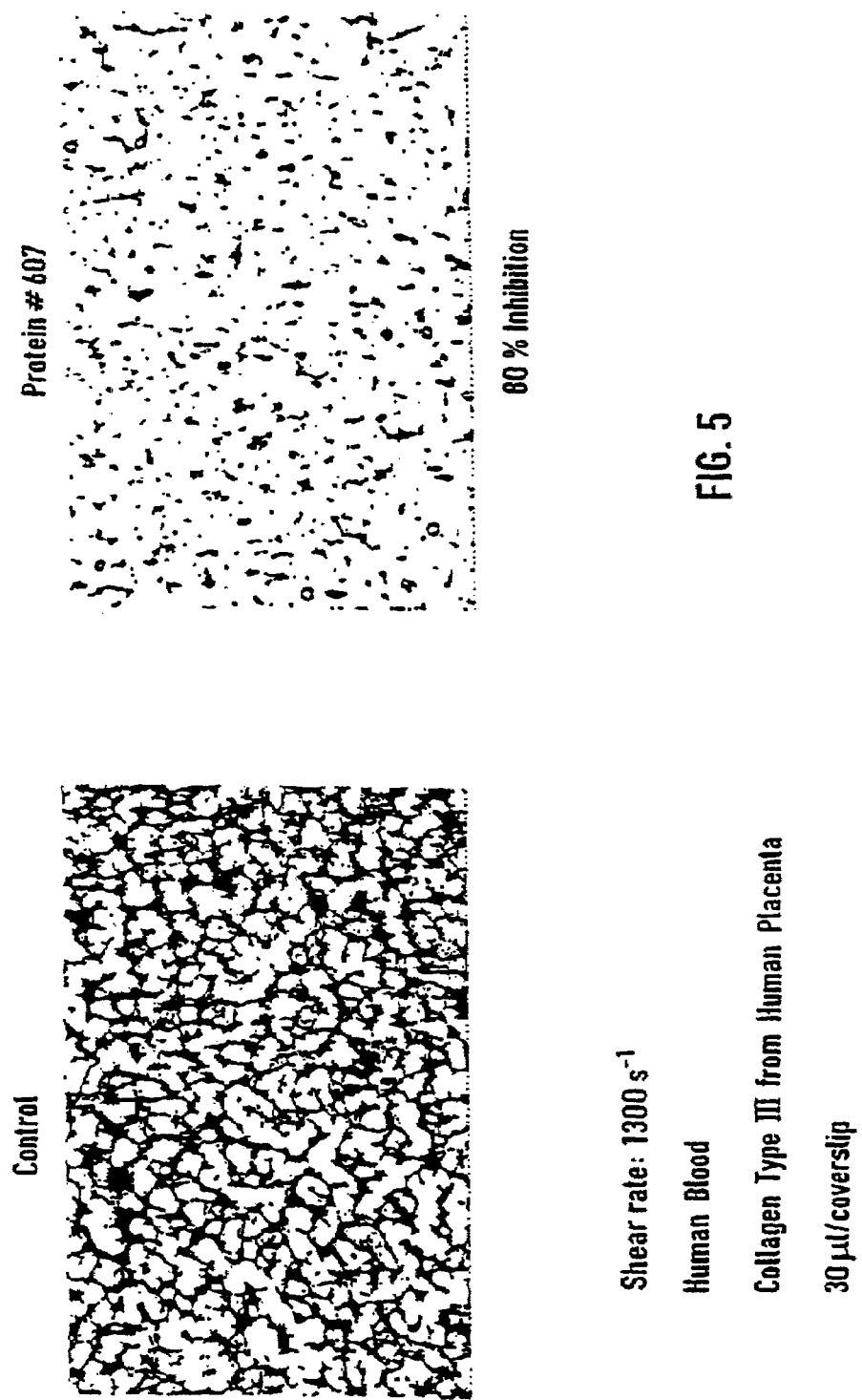

Subsequently, the coverslips are removed, washed in PBS and fixed in 0.25% gluteraldehyde for 30 min., and thereafter stained with May-Grünwald Giemsa. FIG. 9 shows a typical expamle. Extensive coverage with stained platelets is seen in the untreated control surface. A comparable surface pretreated with Saratin shows dramatically deminished (by 80%) platelet binding. Platelet adhesion was quantified with a light microscope as shown in FIG. 5 (magnification ×1000) coupled to a computerized image analyzer (Leica). Results were expressed as the percentage of the surface covered with platelets and platelet aggregates.

Figure 6:
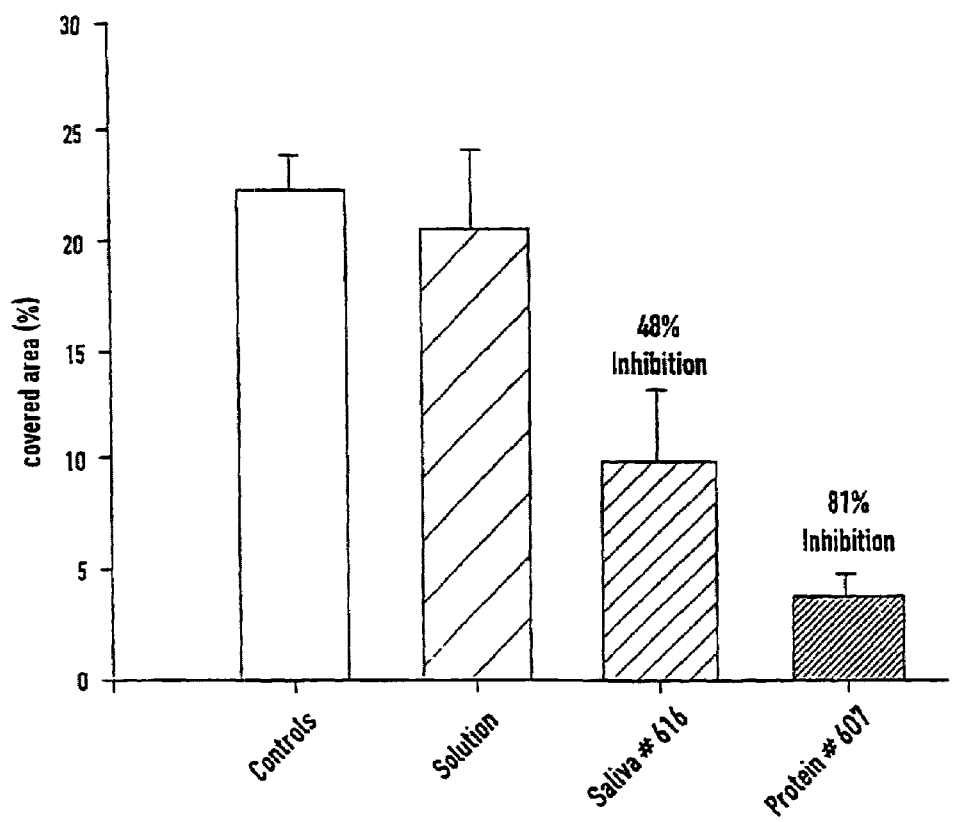
Figure 7:
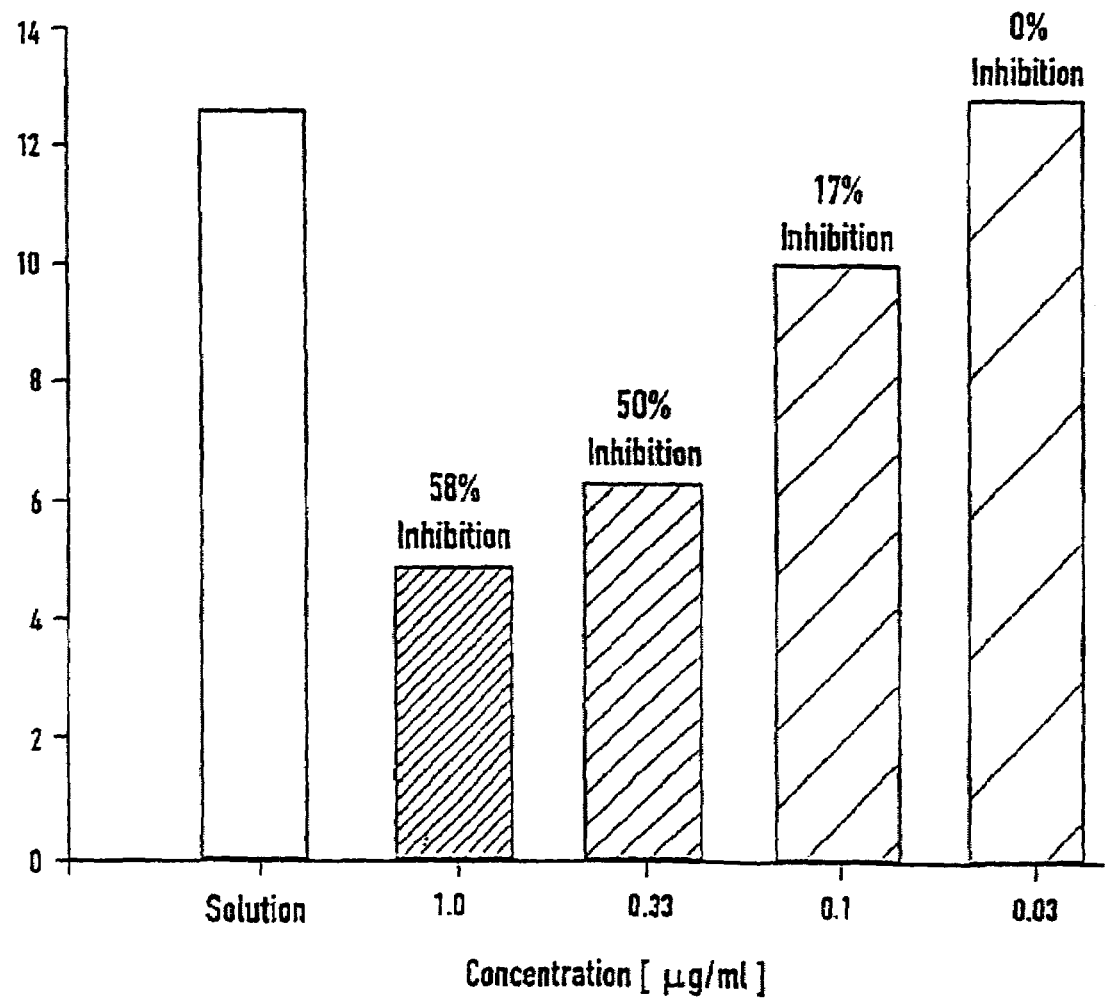

Comparison of saliva inhibitory activity has been compared to purified protein as demonstrated in FIG. 6. Platelet adhesion on collagen type III coated coverslips at a shear rate of 1300 s−1 with crude saliva (#616) produced an inhibition of about 48% compared to control. Purified protein (#607; Saratin) demonstrated a reduction in platelet deposition of about 81% at standardized protein concentrations. The inhibition induced by Saratin increases in a dose-dependent manner with higher concentrations of purified protein as demonstrated in FIG. 7.

Example 10

Immunization and Antibodies

With the first lot of highly purified natural protein available, immunization of animals has been started right away. Immune sera were raised in rabbits and high titered reagents were available for further screening. Additional antisera became available when the peptide sequence of the complete protein was available and three synthetic peptides have been synthesized (amino-acid sequence 83–103, 13–30, 58–69) coupled to KLH with a standard linker procedure and used for immunization. Three sera directed to an N-terminal peptide segment and two sera specific for C-terminal peptides have established. With the high titered immune sera available it has been possible to establish and use Elisa technology to monitor and quantitate purification of naturally purified as well as recombinant protein. Thus the time consuming and rather work intensive platelet-inhibition assay could be replaced and was applyed only to confirm the inhibitory potential of finally purified protein.

Example 11

Immuno-Assays for Estimation of Saratin Binding

Acidified Horm-collagen (Nycomed) has been used for the coating of 96-well micro-titer plates (Nunc) 50 µl of the collagen solution (20 µg/ml) has been used to coat plates over night. Prior to testing the plates have been washed three times with PBS and have been incubated with a BSA solution (1%) in order to prevent non-specific adhesion. 50 µl Saratin has been added in serial delution and have been incubated for one hour. Plates were washed three times prior to the application of anti-Saratin antibody for detection. After an additional one our incubation step surplus antibody has been removed and a second biotin-labeled Antibody has been used for detection. Read-out has been performed via streptavidin-POD catalyzed colour reaction with substrates such as ODB-tablets (Dako) measured at 490 nm.

Example 12

Competition Assay for Screening Inhibitors

Recombinant tagged Saratin (His-tag) prepared as described in Example 7 has been compared with native untagged Saratin for collagen binding. Plates coated with acidified Horm-collagen (Nycomed) have been prepared as decribend in Example 11. Detection was performed with rabbit anti-Saratin antibodies. The taggged and untagged Saratins showed identical binding properties. Alternatively the untagged Saratin version has been modified by biotinylation (Pierce, biotinylation kit) and compared to unmodified Saratin. Binding properties to collagen have been identical. Futhermore experiments have been performed using the biotinylated Saratin to cross-compete with unmodified Saratin, peptides, saliva derived Saratin, complete saliva or antibodies directed to Saratin. Binding of the various "competitors" to collagen has been tested by estimating the binding of biotinylated Saratin using a streptavidine-POD conjugate and ODB-substrate reaction for detection. This assay comprising biotinylated Saratin was typically used for the estimation of Saratin concentration in saliva (750 µg/l), epitope mapping of Saratin directed antibodies, evaluation of bioactive Saratin, mutated Saratin. In order to explore the potential of the assay blocking as well as none blocking anti-Saratin antibodies raised with specific Saratin peptides have been used.

Example 13

Yeast Expression Vector and Expression

Figure 8:
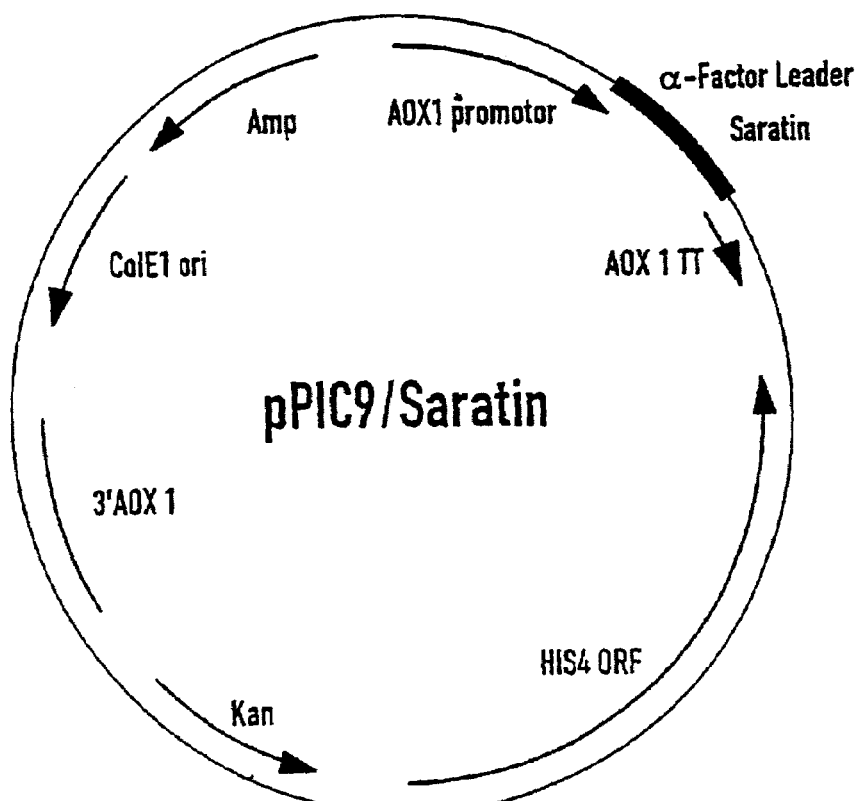

The *pichia* multi copy expression system (Invitrogen) has been used as a typical example for yeast expression. The construction of the yeast expression vector is shown in FIG. 8. For generation of the expression vector for Saratin the PCR amplification method has been used to generate restriction ends (5' EcoR I, 3' Not 1) compatible with the ligation into the appropriate vector (pPIC9K). The following 5'-primer09 and the 3'-primer10.

Before transforming the *Pichia* spheroplasts the expression vector has been linearized with Sal I. Colonies have been screened for His$^+$ Mut$^+$-positiv mutants to ensure integration of the Saratin gene. Typical growing conditions have been: 28–30° C., up to an optical density of OD 2–6. Induction of expression was performed after resupending centrifuged cells in medium and addition of methanol up to a final concentration of 0.5% and maintaining this condition for an extented time period which typically would be 24 hours. After a typical fermentation period of 6 days the product was recovered from the supernatant and analysed by SDS-PAGE and ELISA.

---

The invention claimed is:

1. A method of identifying compounds that compete with the binding of Saratin to collagen, comprising:
   determining the binding of said Saratin to collagen in the presence or absence of a competitor.

2. The method of claim 1 wherein said Saratin is the same as a polypeptide isolated from *Hirudo medicinalis* and has a molecular weight of about 12,000±1 kD.

3. The method of claim 1, wherein said Saratin is biotinylated Saratin.

4. The method of claim 1, wherein said Saratin comprises the amino acid sequence set forth in SEQ ID NO:2.

5. The method of claim 1, wherein said competitor is an antibody.

6. The method of claim 1, wherein said competitor is a blocking anti-Saratin antibody.

* * * * *